(12) United States Patent
Sedan (10) Patent No.: US 9,342,654 B2
(45) Date of Patent: May 17, 2016

(54) ENCODING HIGH QUALITY (MEDICAL) IMAGES USING STANDARD LOWER QUALITY (WEB) IMAGE FORMATS

(71) Applicant: KONINKLIJKE PHILIPS N.V., Eindhoven (NL)

(72) Inventor: Boaz Sedan, Palo Alto, CA (US)

(73) Assignee: Koninklijke Philips N.V., Eindhoven (NL)

( * ) Notice: Subject to any disclaimer, the term of this patent is extended or adjusted under 35 U.S.C. 154(b) by 118 days.

(21) Appl. No.: 14/359,218

(22) PCT Filed: Nov. 16, 2012

(86) PCT No.: PCT/IB2012/056499
§ 371 (c)(1),
(2) Date: May 19, 2014

(87) PCT Pub. No.: WO2013/072889
PCT Pub. Date: May 23, 2013

(65) Prior Publication Data
US 2014/0341450 A1 Nov. 20, 2014

Related U.S. Application Data

(60) Provisional application No. 61/581,259, filed on Dec. 29, 2011, provisional application No. 61/561,429, filed on Nov. 18, 2011.

(51) Int. Cl.
| | | |
|---|---|---|
| G06K 9/00 | (2006.01) |
| G06F 19/00 | (2011.01) |
| H04N 19/70 | (2014.01) |
| H04N 19/44 | (2014.01) |

(52) U.S. Cl.
CPC .............. *G06F 19/321* (2013.01); *H04N 19/44* (2014.11); *H04N 19/70* (2014.11)

(58) Field of Classification Search
None
See application file for complete search history.

(56) References Cited

U.S. PATENT DOCUMENTS

| | | | |
|---|---|---|---|
| 5,614,957 A | 3/1997 | Boyce et al. |
| 2007/0217704 A1 | 9/2007 | Zeng et al. |

FOREIGN PATENT DOCUMENTS

| | | |
|---|---|---|
| EP | 973339 A2 | 1/2000 |
| EP | 1465418 A1 | 10/2004 |
| EP | 2458882 A1 | 5/2012 |
| WO | 2004045217 A1 | 5/2004 |
| WO | 2007082562 A2 | 4/2007 |

OTHER PUBLICATIONS

Wiggins, R. et al. "Image File Formats: past, Present and Future1", Radiographics, vol. 21, May 1, 2001, pp. 789-798.
Celik, M. et al. "Level-Successive Encoding for Digital Photography". IST 2003 PICS Conference, May 13, 2003, pp. 330-334.

*Primary Examiner* — Atiba O Fitzpatrick (57) ABSTRACT

A system for encoding web accessible high quality medical images (5) includes one or more processors (45) and one or more servers (14). The one or more processors a reprogrammed to divide (54) the high quality medical image into multiple 8 bit files (12) by bit location in each pixel of the high quality medical image (5) and padding bits in each file to total 8 bits where the divided number of bits from the high quality medical is less than 8 bits. The one or more processors compress (56) each 8 bit file. The one or more servers (14) are configured to send the compressed files in response to a hyper-text transport protocol(HTTP) request for the high quality medical image (5).

15 Claims, 8 Drawing Sheets

ENCODING HIGH QUALITY (MEDICAL) IMAGES USING STANDARD LOWER QUALITY (WEB) IMAGE FORMATS

This application is a national stage application under 35 U.S.C. §371 of International Application No. PCT/IB2012/056499 filed on Nov. 16, 2012 and published in the English language on May 23, 2013 as International Publication No. WO/2013/072889, which claims priority to U.S. Application No. 61/581,259 filed on Dec. 29, 2011 and U.S. Application No. 61/561,429 filed on Nov. 18, 2011, the entire disclosures of which are incorporated herein by reference.

This application claims the benefit of U.S. provisional application serial no. 61/561,429 filed Nov. 18, 2011, which is incorporated herein in whole by reference.

The present application relates generally to medical imaging. It finds particular application in conjunction with the encoding, transmission and display of high quality medical images, and will be described with particular reference thereto. However, it will be understood that it also finds application in other usage scenarios and is not necessarily limited to the aforementioned application.

High quality medical images are generated from a variety of sources such as magnetic resonance scanners, CT scanners, PET scanners, SPECT scanners, etc. The high quality medical images are stored in formats with bit depths up to 16 bits. A standard medical imaging format such as DICOM includes bit depths as large as 16 bits. Historically the high quality images are viewed with displays which utilize the full bit depth of the generated medical image. The quality of the medical image is important in displaying a consistent high quality image important for comparing with other images and in making a patient diagnosis.

Healthcare practitioners are increasingly mobile, and display technologies have improved and decreased in size. Many small computing devices today carried by healthcare practitioners are capable of viewing high quality images. However, typically devices are not configured for the specialized access methods used to obtain high quality images or handling of native formats. Most computing devices carried by healthcare practitioners are based on Internet technology which favors 8 bit images such as JPEG, TIF, GIF PNG and the like. The computing devices use generalized low cost market oriented computing devices such as tablets, laptops, handheld computing devices, etc. Web browsers such as Internet Explorer, Safari, Firefox, etc., are delivered as standard software on these devices and use standard decompression algorithms or decoders in the retrieving and displaying images such as JPEG, TIF, GIF, PNG, and the like. The Internet technology is primarily based on 8 bit image files and focused on reducing the total size of a file and increasing accessibility through standardized formats. Standard compression techniques include lossless and lossy compression. Lossy compression typically includes the loss of data which results in lower resolution images. Some lossy compression routines parameterize the amount of loss versus the reduction of file size such as JPEG.

Combining new formats into standard browser technology present the difficulty and the expense of deploying and managing customize software in a broad public market. Installing separate applications to transfer and display high quality medical images is impracticable. Even if software were available to perform the transfer and display the high quality medical images, integration with normal workflow of the healthcare practitioner is difficult. Software installation and maintenace on a variety of different computing devices across a variety of organizations is expensive and difficult. Changes made to the computing devices and healthcare systems cause constant management, testing, and modification of any custom software.

The present application discloses a new and improved encoding of high quality medical images which addresses the above referenced matters, and others.

In accordance with one aspect, a system for encoding web accessible high quality medical images includes one or more processors and one or more servers. The one or more processors are programmed to divide the high quality medical image into multiple 8 bit files by bit location in each pixel of the high quality medical image and padding bits in each file to total 8 bits where the divided number of bits from the high quality medical is less than 8 bits. The one or more processors compress each 8 bit file. The one or more servers are configured to send the compressed files in response to a hyper-text transport protocol (HTTP) request for the high quality medical image.

In accordance with another aspect, a method for encoding high quality medical images includes dividing the high quality medical image into multiple 8 bit files by bit location in each pixel of the high quality medical image and padding bits in each file to total 8 bits where the divided number of bits from the high quality medical is less than 8 bits. Each 8 bit file is compressed. Each compressed file is stored accessible by a server.

In accordance with another aspect, a method of encoding/decoding high quality medical images includes dividing a high quality medical image into multiple 8 bit files by bit location in each pixel of the high quality medical image and padding bits in each file to total 8 bits where the divided number of bits from the high quality medical is less than 8 bits. Each 8 bit file is compressed using a standard web-based digital image compression format. Each 8 bit file is downloaded on a computing device using a web-based browser which decompresses each file. The high quality medical image is reassembled by aligning the bits contained in each 8 bit file with the original bit location in the high quality medical image and removing any padded bits. The reassembled high quality medical image is displayed on a display of the computing device.

One advantage resides in standard configured web browsers used to transmit and decompress high quality medical images.

Another advantage is that image quality can be maintained even with standard lossy compression.

Another advantage resides in ease of deployment.

Another advantage includes a mix of compression types.

Another advantage resides in operating within a typical standard computing device installation and configuration.

Another advantage is the accessibility of high quality images on common computing devices.

Another advantage resides in no dependence on an image size.

Still further advantages of the present application will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
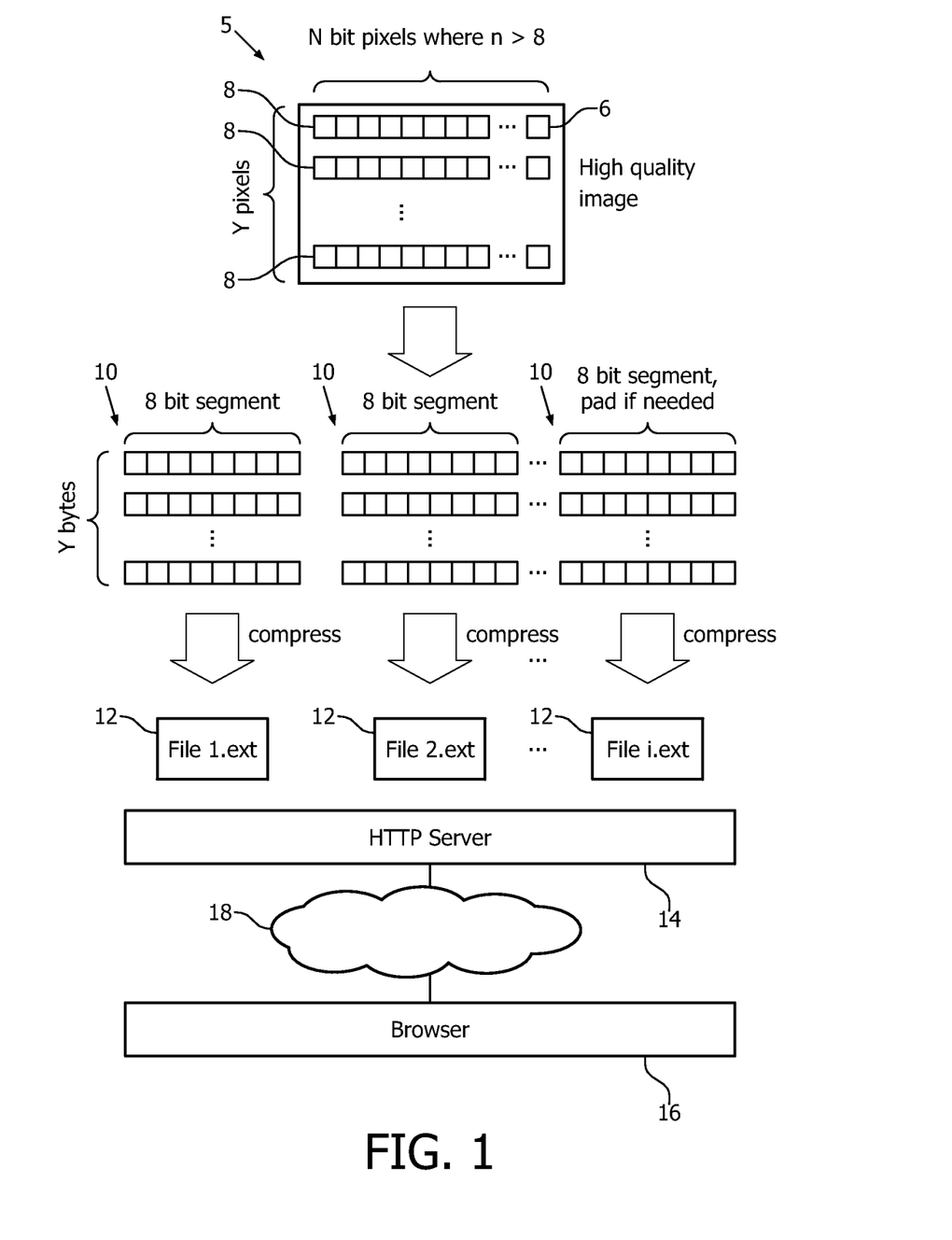
FIG. 1 schematically illustrates an embodiment of encoding a high quality medical image transmitted to a browser using standard web protocols.

With reference to FIG. 1, an embodiment of encoding a high quality medical image transmitted to a browser using standard web protocols is schematically illustrated. The high quality medical image 5 is represented as an image of Y pixels and N bits 6 per pixel 8. The N bits per pixel in the high quality medical image 5 are typically 9-16 bits. However, the method and system can accommodate an image with N greater than 16 bits. The bits per pixel are referred to as the bit depth. For example, an image of 16 bits per pixel has a bit depth of 16. The high quality medical image 5 can include gray scale or include color. The image can be of any size or number of pixels.

Gray scale images are treated as one image. Color images are treated as multiple images where each color channel represents one high quality medical image. The image bits are ordered from high order to low order. A bit plane is one column or position of bits across all pixels. For example, the $16^{th}$ bit of each pixel represents one bit plane, 15-$16^{th}$ represents two bit planes.

The image is broken into 8 bit segments 10 in an embodiment from high order to low order, where each segment of a pixel is represented as 1 byte. The last low order segment depending upon the number of bits in the image is padded with zero bits in the low order bit planes to make the last image a full 8 bit segment. For example, if the image 5 is 9 bits, then the first segment is the first 8 high order bits of each pixel. The second image includes the remaining 1 bit of the image, and 7 bits padded in the low order bits with zeroed bits to make a second 8 bit segment. Another example, if the image 5 is 12 bits, then the first segment is the first 8 high order bits of each pixel, and the second image includes the remaining 4 bits with 4 zeroed bits appended in the low order position.

Alternative embodiments include different spreading the distribution of image bits where for example, a first segment of a 9 bit image includes 4 of the image bits padded with 4 zeroed bits, and the second segment includes the remaining 5 bits with 3 zeroed bits padded. Other embodiments include segmenting from the low order bits to the high order bits. Alternative embodiments include using other bits patterns for padding such as bits set to 1.

In the embodiment of FIG. 1, lossless compression is shown. The high quality medical image 5 is broken into 8 bit segments 10. Each 8 bit segment of Y pixels is compressed using a lossless compression into a file 12 such as a TIFF, GIF, PNG, and lossless JPEG compression. The compressed files 12 are stored on a Hyper-Text Transfer Protocol configured server 14 available for download from a web brower 16. High quality medical images 5 of bit depth 16 or less can be encoded as two files. The number of files for lossless compression is represented by S=integer (N/8) if N mod (8)=0, otherwise S=integer (N/8)+1.

In alternative embodiments when the last segment includes a small number of remaining low order bits, no file is created and the bits are acceptable loss. For example, in a 9 bit file, a first file includes the compressed first 8 high order bits. The remaining bit is acceptable loss and is not encoded.

The compressed files are transmitted from the server via a network 18 to the computing device of a healthcare practitioner. The computing device of the healthcare practitioner includes desktop computers, laptops, tablets, and smart phone devices.

Figure 2:
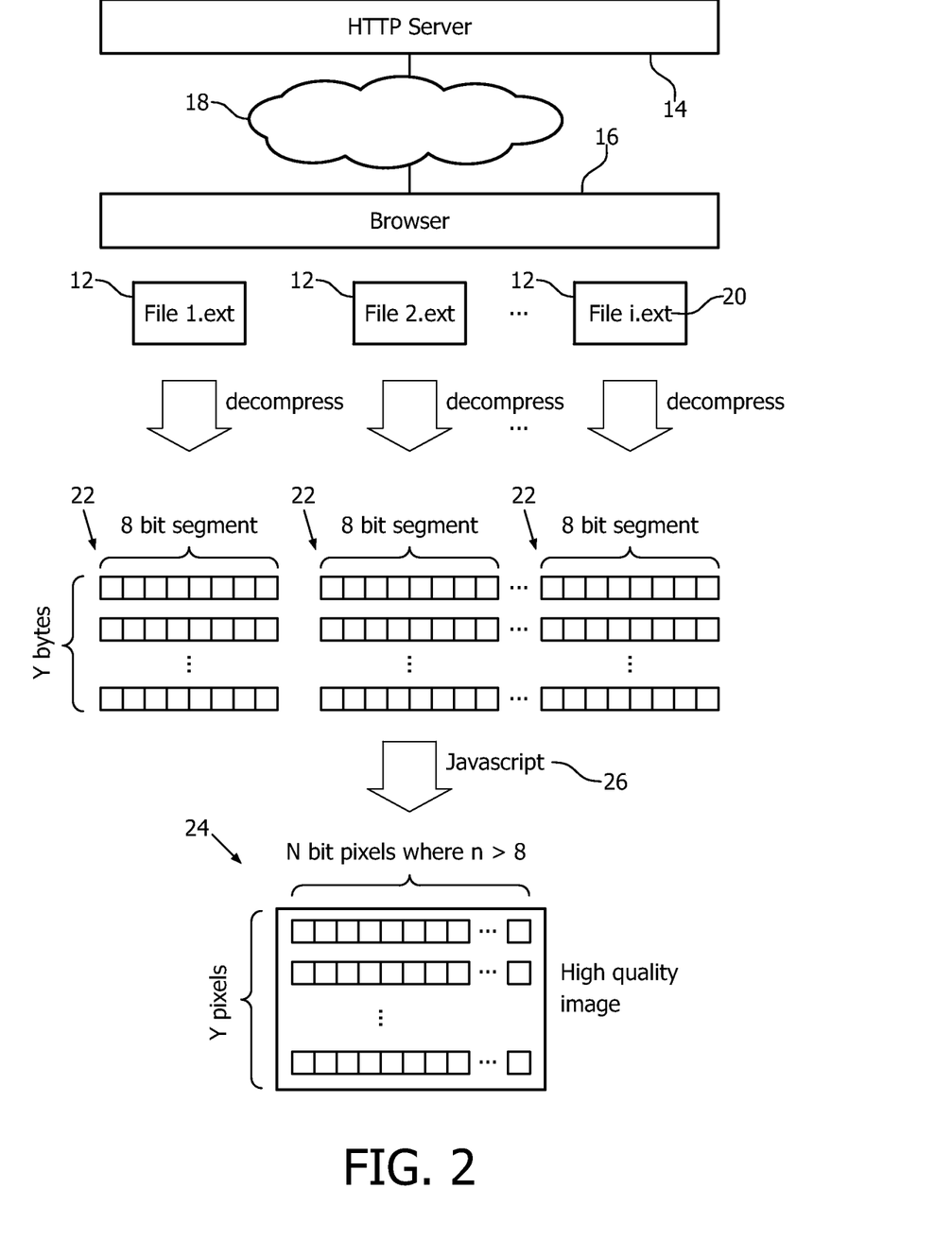
FIG. 2 schematically illustrates an embodiment of decoding an encoded high quality image transmitted to a browser using standard web protocols.

With reference to FIG. 2, an embodiment of decoding an encoded high quality image transmitted to a browser using standard web protocols is schematically illustrated. The computing device are installed and configured with standard browser implementations 16 such as Internet Explorer, Safari, Firefox, Chrome, Opera, etc. The browser 16 communicates with the server 14 via network 18 such as a wired network, wireless network, private network, public network, the Internet, or some combination. The browser 16 configuration includes standard decompression codecs such as PNG, GIF, TIF, and JPEG which automatically decompress received files 12 with standard file extensions 20.

The file information regarding the files 12 including the high quality medical image 5 and the bit organization with the transmitted files are transferred outside of the file encodings. The browser 16 receives the series of files 12 in response to a web based request for the high quality medical image 5 and decompresses each compressed file 12 into a decompressed file 22 using standard codecs.

After decompression of the files 12, the decompressed files 22 are intercepted before display and reassembled into a high quality medical image 24. A standard web programming language program 26 such as a javascript program operates within the native configuration of the computing device. The program 26 orders the bits from each decompressed file 22, strips any padded zeroed bits, and appends the segments into each of Y, N bit pixels of the high quality medical image. The reassembled high quality medical image 24 is displayed on the display of the computing device. The display can be within a browser 12 display or outside of the browser window.

Figure 3:
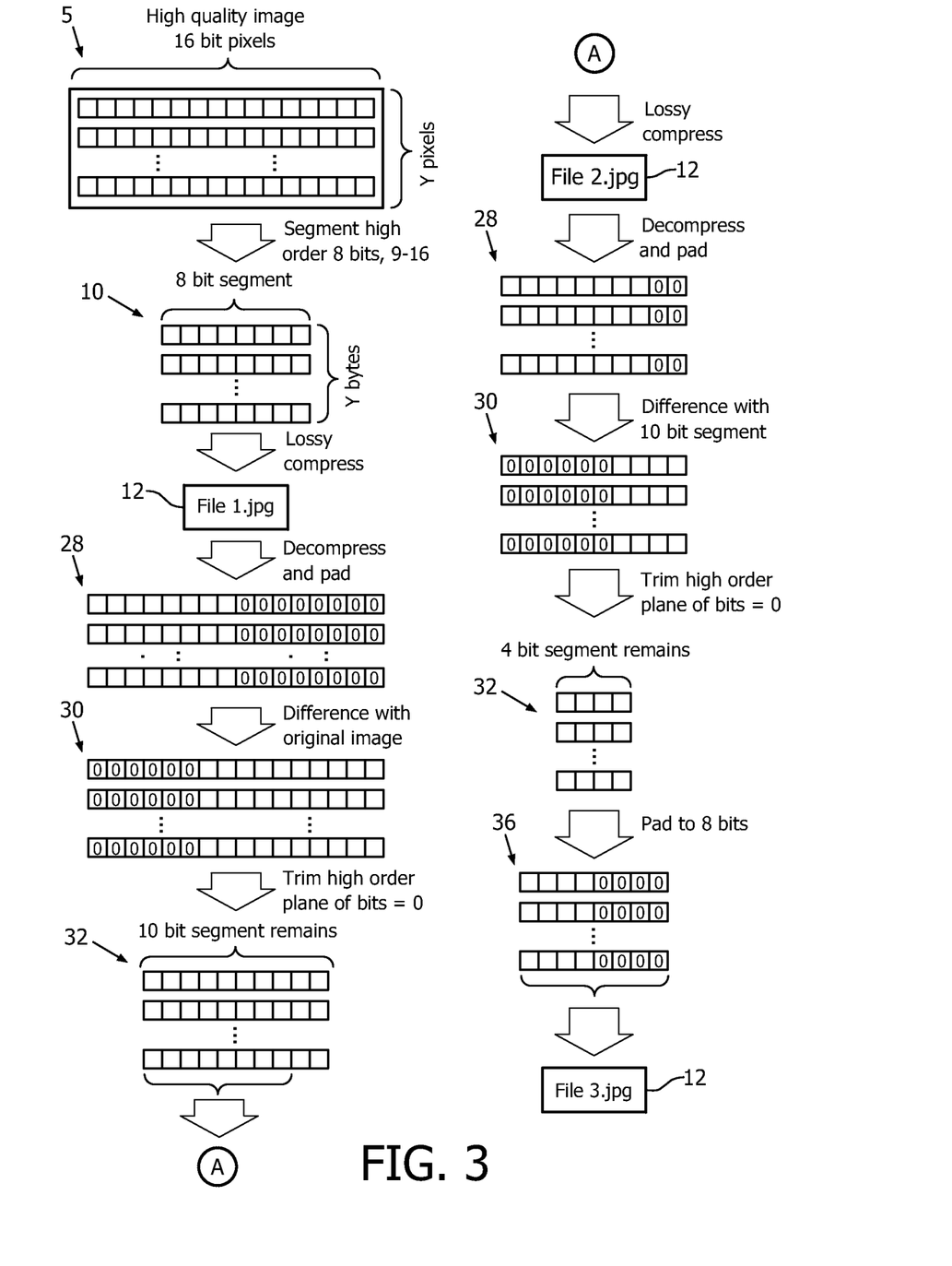
FIG. 3 schematically illustrates an example of encoding a 16-bit high quality image with lossy compression.

With reference to FIG. 3 an example of encoding a 16-bit high quality image with lossy compression is illustrated. The high quality image 5 of bit depth 16 is segmented 10 from high order to low order. The first 8 high order bits are compressed into a file using a lossy compression such as JPEG. The first file 12 is stored for transmission in response to the web browser request for the high quality medical image. A compressed 8 bit file is decompressed and padded with low order zeroed bits. A padded decompressed file 28 is subtracted from the high quality medical image 5. The resulting difference file 30 is trimmed of high order bit planes which are all zeros. The bits 11-16 of each pixel or bit planes 11-16 are all zeros. The zeroed high order bit planes are removed leaving a 10 bit remainder 32 which includes the low order image and the error from the lossy compression of the high order segment.

Of the 10 bit remainder file 32, the next high order 8 bits are compressed into a second file 12. In the example, the compression is a lossy compression. The second file is decompressed and padded with two zeroed low order bits. The decompressed padded second file 28 is subtracted from the 10 bit remainder giving a 10 bit difference file 30. The high order zeroed bit planes are trimmed leaving a 4 bit segment 32.

The 4 bit segment 32 is padded in the low order with zeroed bits to comprising 8 bits. The 8 bit file 36 is compressed into a $3^{rd}$ file 12. Even with lossy compression, by encoding the remainder in a next segment, the loss is carried forward. The lossy compression is restricted to provide no more than several bits of error loss in a trade off to the number of files needed to encode the image. The error loss is carried forward into the next file.

Figure 4:
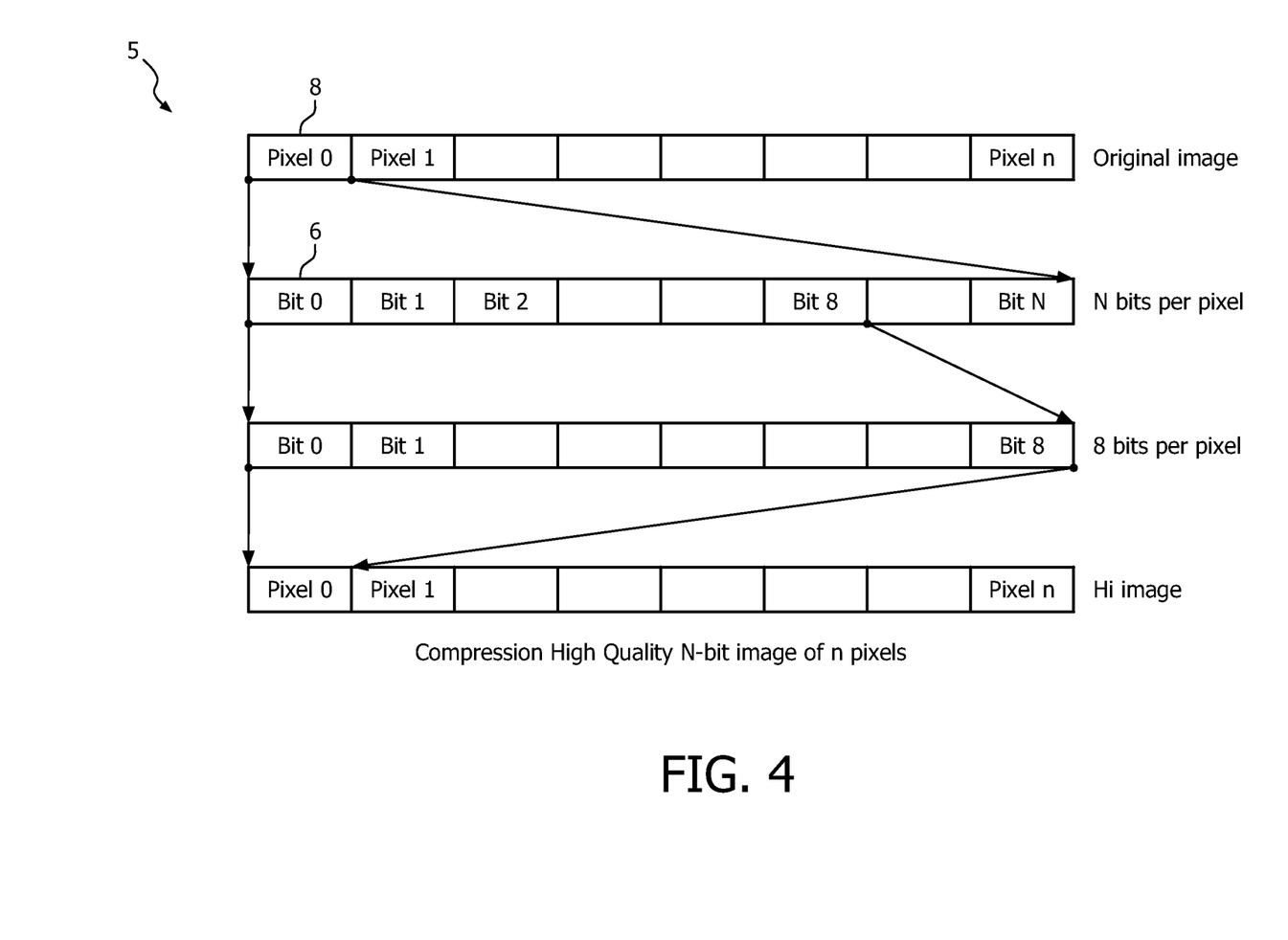
FIG. 4 diagrammatically illustrates the compression of high order image of a high quality image of n-pixels and N-bit depth.

With reference to FIG. 4 the compression of high order image of a high quality image 5 of n-pixels and N-bit depth is diagrammatically illustrated. The system and method is expandable to any bit depth and operates independently of the number of pixels in the high quality medical image. Each pixel 8 includes N bits 6. The first 8 bit segment from the high order bits is referred to as the hi image. The hi image is compressed.

The compression such as JPEG, TIF, PNG can be different for each 8 bit segment 22. For lossless compression, no bits are carried forward. For lossy compression, the error bits are carried forward to the next file.

Figure 5:
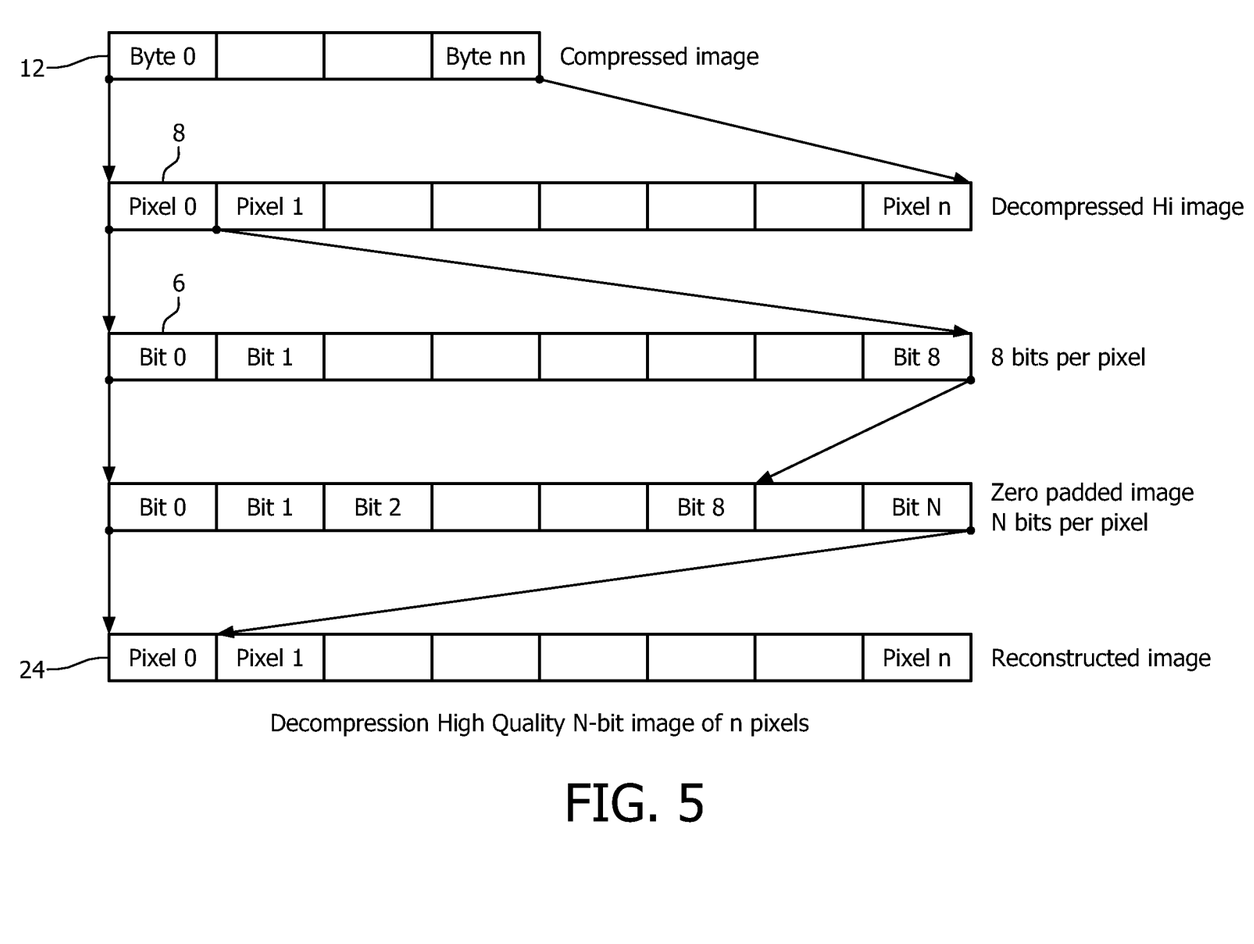
FIG. 5 diagrammatically illustrates the decompression of high order image of a high quality image of n-pixels and N-bit depth.

FIG. 5 the decompression of high order image of a high quality image of n-pixels and N-bit depth is diagrammatically illustrated. The compressed file is decompressed by a standard codec of the web browser 16 based on the file extension 20. A Hi image compressed file includes nn bytes which are expanded through decompression to n bytes or 1 byte per pixel. Each byte of the decompressed Hi image file includes 8 bits. The 8 bits are padded with zeroed low order bits to the orginal pixel size of N bits.

The other files are padded with lower order zeroed bits on the low order to achieve proper alignment and padded with high order zeroed bits to N bits. The Hi image file is added to the other decompressed and properly padded files in which the resulting file is the high order medical image 24 reconstructed.

Figure 6:
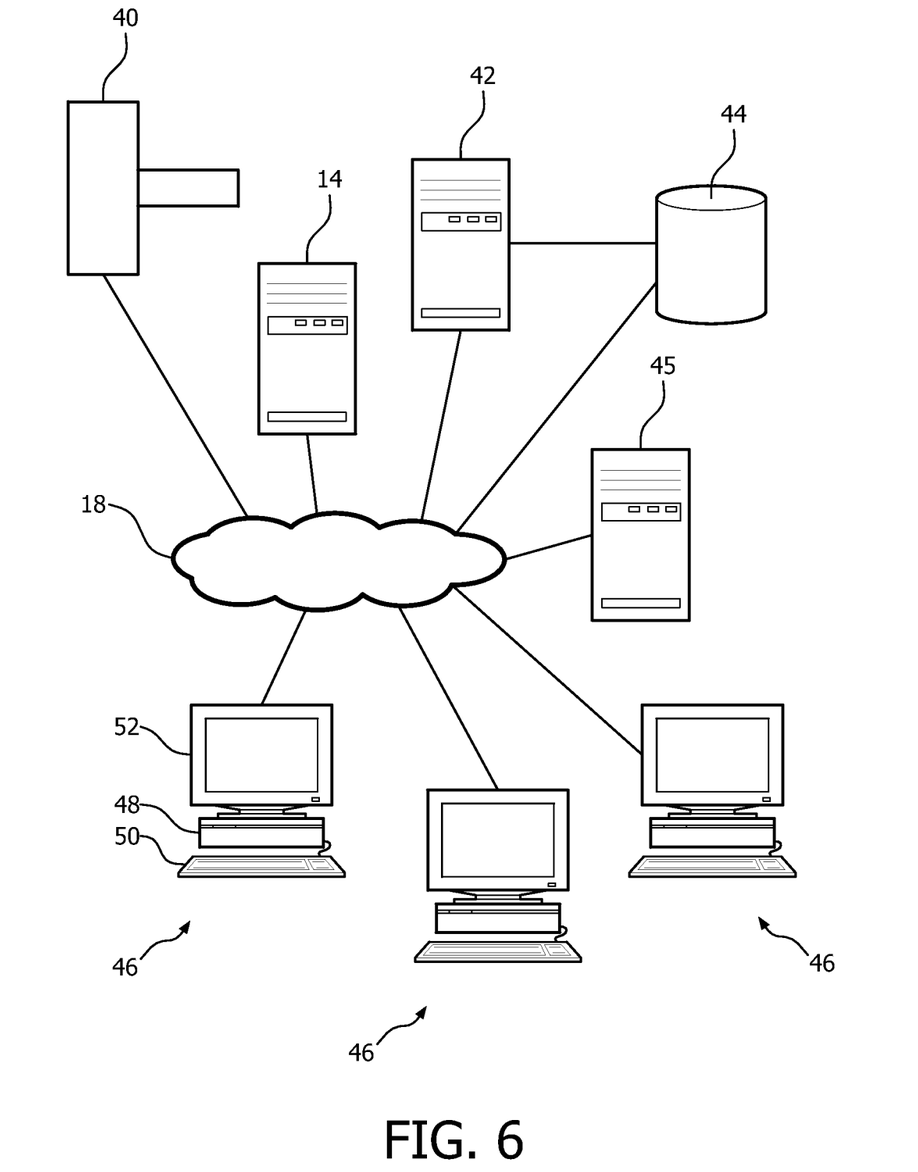
FIG. 6 schematically illustrates the components use in encoding a high quality medical image in one embodiment.

With reference to FIG. 6 the components use in encoding the high quality medical image 5 are shown in one embodiment. The high quality medical images 5 are created from a medical imaging device 40 such as a magnetic resonance scanner, a PET scanner, a SPECT scanner, and the like. The high quality medical image 5 is stored in a storage system 42 such as a Picture Archiving and Communication System (PACS), a cloud-based Radiology Imaging System (RIS), and the like. The storage of images is managed by some database management system which stores images. The images are available to the HTTP configured server 14 either as part of the PACS or RIS system or directly to the image storage 44.

The HTTP configured server 14 retrieves the high quality medical image 5 according to a request from one of a plurality of computing devices 46 operated by healthcare practitioners. The requests include HTTP formatted transaction which request the high quality medical image 5. A server 45 includes one or more processors programmed to encode the high quality medical image 5 as the series of files 12. The server 45 can be combined with the web server 14 or storage system 42.

The computing devices 46 operated by the healthcare practitioners include one or more processors 48 configured to operate at least one browser. The computing devices include at least one input device 50 such as touch pads, pointing devices, keyboards, and the like. The computing devices 46 include at least one display 52 which displays the high quality medical image. The display includes a pixel format which determines the resolution of the computing device.

Figure 7:
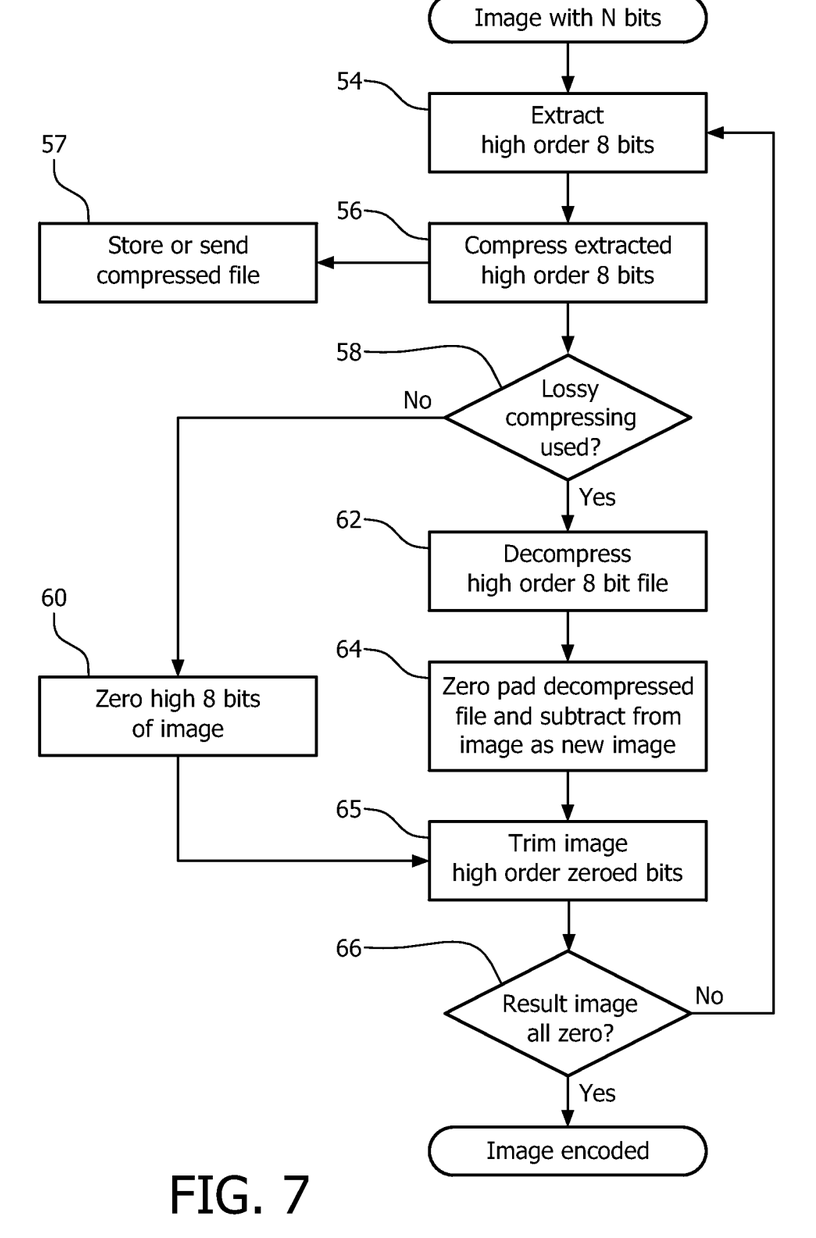
FIG. 7 flowcharts an embodiment of encoding a high quality medical image.

With reference to FIG. 7 an embodiment of encoding the high quality medical image 5 is flowcharted. In a step 54, the high order 8 bits are extracted from the image. In a step 56, the high order 8 bits are compressed and stored as a file. A next step 58 checks the compression for lossy compression. If lossless compression was used, then in a step 60, the high order 8 bits are all zeroed. If a lossy compress was used, then in a step 62, the compressed high order 8 bit file is decompressed. In a next step 64, the decompressed high ordered 8 bit file is padded with zeroed bits to N bits and substracted from the original image. The resulting image replaces the high quality medical image.

In a step 65, the high order bit planes of the resulting image are trimmed of zeroed bits. If bits remain, then the method returns to the step 54 where the high order 8 bits are extracted. If the remaining bits are less than 8 bits, then the bits are padded on the low order with zeroed bits to 8 bits before returning to the step 54.

Figure 8:
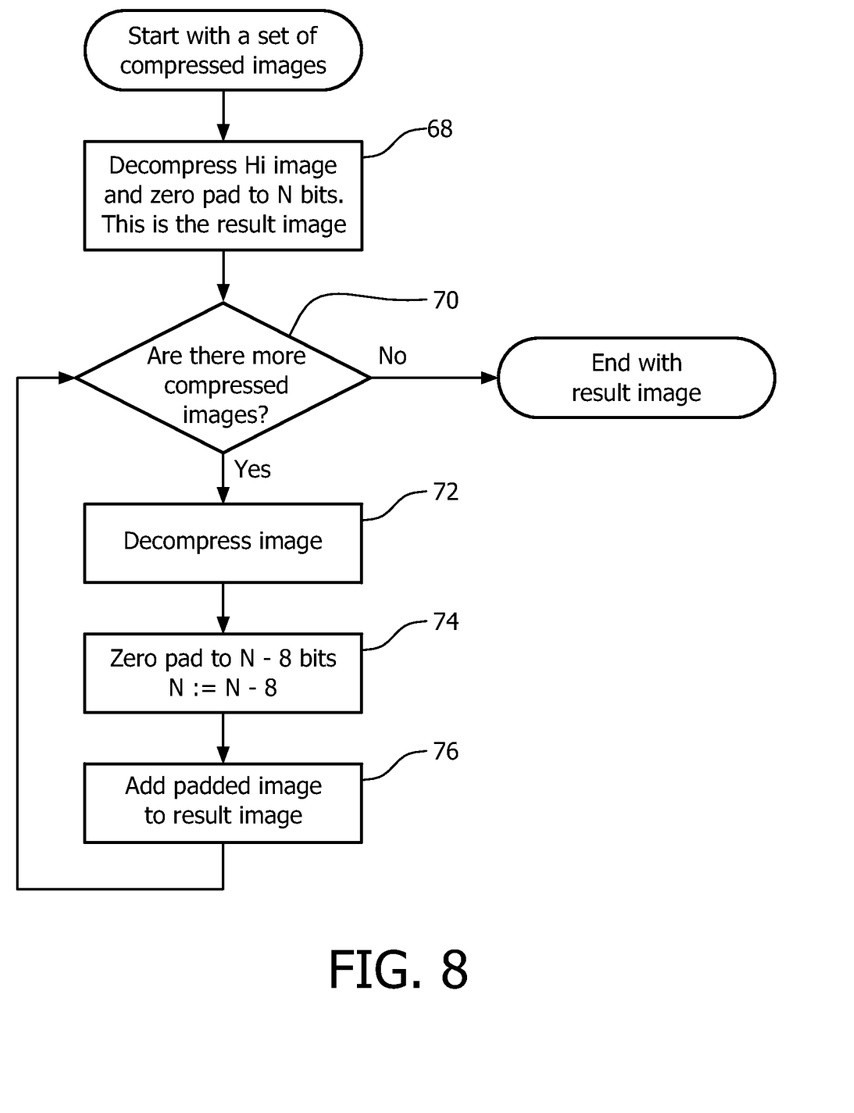
FIG. 8 flowcharts an embodiment of decoding a high quality medical image.

With reference to FIG. 8, an embodiment of decoding a high quality medical image 5 is flowcharted. The method begins with the set of files received by the browser. In a step 68, the first file is decompressed by the appropriate standard codec based on the file type which includes the Hi image and padded to N bits to form the resulting image. If there are more files, then each file is decompressed by the appropriate standard codec in a step 72. Each decompressed file in a step 74 is padded with lower order zeroed bits for proper alignment, and then padded with zeroed high ordered bits for N bits total. The padded decompressed file is added to the resulting image in a step 76 which forms a new resulting image. After each file is decompressed and added to the resulting file and no more files exist, the resulting image is the high quality medical image to be displayed.

It is to be appreciated that in connection with the particular exemplary embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A system for encoding high quality medical images for transmission using standard web protcols, comprising:
one or more processors programmed to:
divide a high quality medical image into multiple 8 bit files, said medical image having a number of pixels (Y) and each pixel having a number of bits (N) ordered from a high order to a low order, wherein the high quality medical image is broken into 8 bit segments from high order bits to low order bits of each pixel of the high quality medical image and each 8 bit segment of Y pixels is compressed into an 8 bit file, wherein each segment of a pixel is represented as 1 byte and padded with bits to total 8 bits where the number of bits is less than 8 bits;
compress at least one 8 bit file with a lossy compression;
decompress the at least one 8 bit file;
compute the difference between the at least one decompressed 8 bit file and the at least one 8 bit file before lossy compression;
replace the bits located in the original high quality medical image with the difference between the decompressed file and the file before compression trimmed by removing each high order bit plane location which include all zero bits, wherein the bit plane is one column of bits across all pixels,
compress each 8 bit file; and
one or more servers configured to:
send the compressed files in response to a hyper-text transport protocol (HTTP) request for the high quality medical image.

2. The system for encoding high quality medical images for transmission using standard web protocols according to claim 1, wherein the file compression format used to compress each file includes at least one digital image format of:
jpeg;
tif;
gif; and
png.

3. The system for encoding high quality medical images for transmission using standard web protocols according claim 1, further including:
a non-transitory data storage which stores the compressed files before sending using the HTTP configured one or more servers.

4. The system for encoding high quality medical images for transmission using standard web protocols according claim 1, further including:
a picture archiving and retrieval system (PACS) which organizes storage of high quality medical images.

5. The system for encoding high quality medical images for transmission using standard web protocols according claim 1, further including:
a plurality of computing devices, each include:
a browser configured to:
send a HTTP formatted request to download at least one high quality medical image of N bit depth where N is greater than 8; and
decompress 8 bit digital image files; and
one or more processors programmed to assemble the high quality medical image by combining the bits from each decompressed 8 bit file in the proper order for each pixel and padding with low order zeroed bits where needed to total N bits in each pixel; and
a display which displays the high quality medical image.

6. A method for encoding high quality medical images, comprising:
dividing the high quality medical image into multiple 8 bit files, said medical image having a number of pixels (Y) and each pixel having a number of bits (N) ordered from a high order to a low order, wherein the high quality medical image is broken into 8 bit segments from high order bits to low order bits of each pixel of the high quality medical image and each 8 bit segment of Y pixels is compressed into an 8 bit file, wherein each segment of a pixel is represented as 1 byte and padded with bits to total 8 bits where the number of bits is less than 8 bits;
compressing at least one 8 bit file with a lossy compression;
decompressing the at least one 8 bit file;
computing the difference between the at least one decompressed 8 bit file and the at least one 8 bit file before lossy compression;
replacing the bits located in the original high quality medical image with the difference between the decompressed file and the original file trimmed by removing each high order bit plane location which include all zero bits, wherein the bit plane is one column of bits across all pixels;
compressing each 8 bit file;
sending the compressed files in response to a hyper-text transport protocol (HTTP) request for the high quality medical image or storing each compressed file accessible by a server.

7. The method according to claim 6 wherein padding includes appending zeroed bits adjacent to the low order bits.

8. The method according to claim 6 wherein the low order bits of the high quality medical image (5) are not encoded.

9. The method according to claim 6, wherein compressing each file includes multiple compression formats.

10. The method according to claim 6, wherein an accessible server includes a hypertext transport protocol (HTTP) configured server.

11. The method according to claim 6, further including:
receiving each stored 8 bit file on a computing device through a web configured browser which decompresses each 8 bit file;
assembling the high quality medical image by combining the bits contained in each decompressed file in the proper order for each pixel and padding with low order zeroed bits where needed to total N bits in each pixel; and
displaying the high quality medical image on the computing device.

12. A non-transitory computer-readable medium encoded to control one or more processors to perform claim 6.

13. A non-transitory computer-readaable medium storing the compress files of claim 6.

14. A method of decoding high quality medical images, comprising:
downloading 8 bit files of a high quality medical image on a computing device using a web-based browser which decompresses each file in which the high quality medical image was divided into multiple 8 bit files, said medical image having a number of pixels, (Y) and each pixel having a number of bits (N) ordered from a high order to a low order, wherein the high quality medical image is broken into 8 bit segments from high order bits to low order bits of each pixel of the high quality medical image and each 8 bit segment of (Y) pixels is compressed into an 8 bit file, wherein each segment of a pixel is represented as 1 byte and padded to total 8 bits where the number of bits is less than 8 bits and compressed using a standard web-based digital image compression format;

reassembling the high quality medical image by aligning the bits contained in each 8 bit file with the original bit location in the high quality medical image and removing any padded bits; and displaying the reassembled high quality medical image on a display of a computing device.

15. A system for decoding high quality medical images comprising:

one or more processors programmed to perform the method of claim 14; and a display on which the reassembled high quality medical image is display.

* * * * *